United States Patent [19]

Roper

[11] Patent Number: 4,562,297

[45] Date of Patent: Dec. 31, 1985

[54] ALDEHYDE SYNTHESIS

[75] Inventor: Jerry M. Roper, Baton Rouge, La.

[73] Assignee: Ethyl Corporation, Richmond, Va.

[21] Appl. No.: 667,916

[22] Filed: Nov. 2, 1984

Related U.S. Application Data

[63] Continuation-in-part of Ser. No. 412,150, Aug. 27, 1982, abandoned.

[51] Int. Cl.⁴ .................... C07C 45/36; C07C 47/565
[52] U.S. Cl. .................................................. 568/432
[58] Field of Search ............................... 568/431, 432

[56] References Cited

U.S. PATENT DOCUMENTS 3,435,061  3/1969  Grasselli et al. ................ 568/431 X
4,009,210  2/1977  Cahoy .

FOREIGN PATENT DOCUMENTS 2363464  10/1981  Fed. Rep. of Germany .

OTHER PUBLICATIONS

Patai, Chemistry of the Carbonyl Group, (1966), 125–127 & 170.
Miller et al., Jour. Amer. Chem. Soc., vol. 78, (1956), 1017–1034.

*Primary Examiner*—Bernard Helfin
*Attorney, Agent, or Firm*—Donald L. Johnson; John F. Sieberth; Patricia J. Hogan

[57] ABSTRACT

3,5-Dihydrocarbyl-4-hydroxybenzaldehydes are prepared by intimately contacting a 4-(1-alkenyl)-2,5-dihydrocarbylphenol, such as 1,1-dimethyl-2-(3,5-di-t-butyl-4-hydroxyphenyl)ethene, with at least a stoichiometric amount of an oxygen-containing gas at about 50°–25° C. in the presence of an alcohol solvent and a catalytic amount of an alkali or alkaline earth metal hydroxide.

14 Claims, No Drawings

ALDEHYDE SYNTHESIS

CROSS-REFERENCE TO RELATED APPLICATION

This application is a continuation-in-part of copending application Ser. No. 412,150, filed Aug. 27, 1984, now abandoned.

FIELD OF INVENTION

This invention relates to 3,5-dihydrocarbyl-4-hydroxybenzaldehydes and more particularly to a process for preparing them.

BACKGROUND

There are various known techniques of preparing benzaldehydes. Miller et al., *Journal of the American Chemical Society*, Vol. 78, pp. 1017–1034 (1956) and Patai, *The Chemistry of the Carbonyl Group*, Interscience Publishers, pp. 125–127 (1966) show that benzaldehyde is one of the products obtained by the oxidation of styrene. U.S. Pat. No. 3,435,061 (Grasselli et al.) suggest that the poor benzaldehyde yields of Miller et al. and Patai could be improved by conducting the oxidation in the presence of certain catalysts, such as mixed metal oxide catalysts, at 300°–800° C. European Patent Application No. 0 012 939 (Nishizawa et al.) shows that p-cresols can be oxidized to 4-hydroxybenzaldehydes in the presence of at least one equivalent of base and a catalytic amount of cobalt or a cobalt compound. U.S. Pat. No. 4,009,210 (Cahoy) teaches that 3,5-dihydrocarbyl-4-hydroxybenzaldehydes can be prepared by reacting a 2,6-dihydrocarbylphenol with hexamethylenetetramine or a combination of formaldehyde and ammonium acetate in aqueous acetic acid.

SUMMARY OF INVENTION

An object of this invention is to provide a novel process for preparing 3,5-dihydrocarbyl-4-hydroxybenzaldehydes.

Another object is to provide such a process which is capable of providing the products in good yields.

These and other objects are attained by intimately contacting a 4-(1-alkenyl)-2,6-dihydrocarbylphenol with at least a stoichiometric amount of an oxygen-containing gas at about 50°–250° C. in the presence of an alcohol solvent and a catalytic amount of an alkali or alkaline earth metal hydroxide so as to form a 3,5-dihydrocarbyl-4-hydroxybenzaldehyde.

DETAILED DESCRIPTION 4-(1-Alkenyl)-2,6-dihydrocarbylphenols that can be used in the practice of the invention are generally compounds corresponding to the formula:

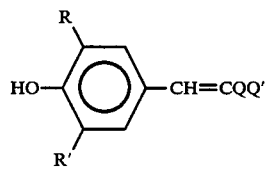

wherein R and R' are independently selected from alkyl, cycloalkyl, and aralkyl groups containing 1–40 carbons and Q and Q' are independently selected from hydrogen and alkyl and alkenyl groups containing 1–40 carbons. The preferred compounds are those in which R and R' are independently selected from alkyl, cycloalkyl, and aralkyl groups containing 1–20 carbons, more preferably 3–8 carbons, Q and Q' are independently selected from hydrogen and alkyl and alkenyl groups containing 1–20 carbons. Such compounds are known and can be prepared, e.g., by the process of German Pat. No. 23 63 464 (Roos et al.), the teachings of which are incorporated herein by reference.

Exemplary of the 4-(1-alkenyl)-2,6-dihydrocarbylphenols that may be employed are 2-(3,5-dihydrocarbyl-4-hydroxyphenyl)ethenes wherein the 3,5-substitution is dimethyl, diisopropyl, di-n-butyl, di-sec-butyl, di-t-butyl, di-sec-octyl, dibenzyl, di-alpha-methylbenzyl, 3-isopropyl-5-methyl, 3-methyl-5-cyclohexyl, 3-methyl-5-benzyl, etc.; the corresponding 1-substituted-2-(3,5-dihydrocarbyl-4-hydroxyphenyl)ethenes wherein the 1-substituent is methyl, ethyl, n-propyl, isopropyl, n-butyl, hex-3-enyl, oct-2-enyl, dec-4-enyl, etc.; the corresponding 1,1-disubstituted-2-(3,5-dihydrocarbyl-4-hydroxyphenyl)ethenes wherein the 1,1-substitution is dimethyl, diethyl, di-n-propyl, diisopropyl, di-n-butyl, dihex-3-enyl, dioct-2-enyl, didec-4-enyl, 1-methyl-1-n-butyl, 1-n-propyl-1-n-butyl, 1-isopropyl-1-hex-3-enyl, 1-n-butyl-1-oct-2-enyl, 1-ethyl-1-dec-4-enyl, etc. A particularly preferred starting material is 1,1-dimethyl-2-(3,5-di-t-butyl-4-hydroxyphenyl)ethene.

The oxygen-containing gas that is reacted with the 4-(1-alkenyl)-2,6-dihydrocarbylphenol may be any such gas but is generally air or oxygen itself. As indicated above, the amount of the gas used should be at least the stoichiometric amount required to cleave the olefinic bond located at the 4-position of the phenyl ring, and an excess is usually employed to accomplish greater conversions and higher yields of product.

The solvent utilized in the reaction may be any alcohol in which the 4-(1-alkenyl)-2,6-dihydrocarbylphenol and catalyst are sufficiently soluble, the alcohols having the greater solvating powers being more effective in producing high yields of product. The alcohols may be aliphatic, cycloaliphatic, aromatic, monohydric, or polyhydric and preferably contain 1–10 carbons. Among the utilizable solvents are methanol, ethanol, isopropyl alcohol, n-propanol, n-butanol, sec-butyl alcohol, t-butyl alcohol, n-pentanol, isopentyl alcohol, n-hexanol, isohexyl alcohol, ethylene glycol, cyclohexanol, phenol, benzyl alcohol, etc. The preferred alcohols are the branched-chain alkanols, such as isopropyl alcohol, t-butyl alcohol, etc. This ingredient is employed in solvent amounts, i.e., amounts sufficient to solvate the other ingredients, but the quantity used is not otherwise critical.

The catalyst used in the reaction is an alkali or alkaline earth metal hydroxide, such as the hydroxides of sodium, potassium, lithium, rubidium, cesium, calcium, barium, and strontium, preferably sodium or potassium hydroxide. Although it is not believed that the use of relatively large amounts of the catalyst would be harmful, it is preferred to use this ingredient in catalytic amounts, e.g., about 0.1–1%, based on the weight of the 4-(1-alkenyl)-2,6-dihydrocarbylphenol.

The reaction is conducted by intimately contacting the 4-(1-alkenyl)-2,6-dihydrocarbylphenol with the oxygen-containing gas in the presence of the solvent and catalyst at a temperature of about 50°–250° C., preferably about 50°–150° C. Typically, the reaction is conducted at atmospheric pressure, but pressures up to about 200 psig may be employed, if desired. The intimate contact is achieved by the use of agitation, as is conventional in chemical reactions. The time required to obtain optimum yields varies with factors such as the reaction temperature, the type and amount of catalyst used, and the particular solvent employed but is frequently in the range of about 1.5-6 hours.

When the reaction has been completed, the product can be easily separated from the reaction mixture by conventional means, such as distillation, recrystallization, etc.

The following examples are given to illustrate the invention and are not intended as a limitation thereof. As used in these examples, DDHPE is a designation for 1,1-dimethyl-2-(3,5-di-t-butyl-4-hydroxyphenyl)ethene, and DHB is a designation for 2,6-di-t-butyl-4-hydroxybenzaldehyde.

COMPARATIVE EXAMPLE A

A suitable reaction vessel was charged with an isopropyl alcohol solution containing about 1.0 mmol of DDHPE and immersed in an oil bath heated to 70°-80° C. An excess of oxygen was bubbled through the stirred reaction mixture for one hour, after which the reaction mixture was cooled and acidified with very dilute sulfuric acid to precipitate the product. The precipitate was dissolved in dichloromethane, dried with anhydrous magnesium sulfate, and concentrated to dryness. GC analysis showed the yield of DHB to be 13 area percent.

COMPARATIVE EXAMPLE B

Comparative Example A was essentially repeated except that about 0.2 mmol of 1,4-diazabicyclo[2.2.2]octane catalyst was added to the DDHPE solution, the oil bath was heated to about 60°-65° C., and the reaction was conducted for two hours. GC analysis showed the yield of DHB to be 16 area percent.

EXAMPLE I

Comparative Example B was essentially repeated except that the catalyst was replaced with an amount of 40% aqueous sodium hydroxide such as to provide 0.2 mmol of sodium hydroxide. The isolated yield of DHB was about 100%.

EXAMPLE II

Example I was essentially repeated except that the reaction temperature was increased to 72°-76° C. and the reaction time was decreased to 1.2 hours. The isolated yield of DHB was 84%.

EXAMPLE III

Three reactions were conducted by essentially repeating Example I except for using different solvents and conducting the reactions for only one hour. The solvents used and DHB yields obtained are shown below.

| Reaction | Solvent | Area % DHB |
| --- | --- | --- |
| III-A | methanol | 60 |
| III-B | ethanol | 80 |
| III-C | t-butyl alcohol | 85 |

EXAMPLE IV

Using the same general procedure as in the preceding example, three reactions were conducted at 68°-72° C. for 1.25 hours using 0.14 mmol of potassium hydroxide (a 40% aqueous solution) and different solvents. The solvents used and DHB yields obtained are shown below.

| Reaction | Solvent | Area % DHB |
| --- | --- | --- |
| IV-A | n-butyl alcohol | 59 |
| IV-B | ethylene glycol | 36 |
| IV-C | benzyl alcohol | 43 |

EXAMPLE V

Using the same general procedure as in the preceding example, three reactions were conducted at 70°-72° C. for 1.2 hours using about 2.2 mmols of calcium hydroxide (a 33% aqueous slurry) and different solvents. The solvents used and DHB yields obtained are shown below.

| Reaction | Solvent | Area % DHB |
| --- | --- | --- |
| V-A | ethanol | 55 |
| V-B | isopropyl alcohol | 51 |
| V-C | phenol | 86 |

It is obvious that many variations can be made in the products and processes set forth above without departing from the spirit and scope of this invention.

I claim:

1. A process which comprises intimately contacting a 4-(1-alkenyl)-2,6-dihydrocarbylphenol with at least a stoichiometric amount of an oxygen-containing gas at about 50°-250° C. in the presence of an alcohol solvent and a catalytic amount of an alkali or alkaline earth metal hydroxide so as to form a 3,5-dihydrocarbyl-4-hydroxybenzaldehyde.

2. The process of claim 1 wherein the 4-(1-alkenyl)-2,6-dihydrocarbylphenol is a compound corresponding to the formula:

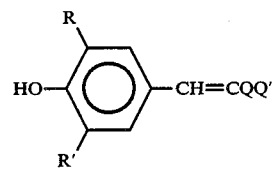

wherein R and R' are independently selected from alkyl, cycloalkyl, and aralkyl groups containing 1-40 carbons and Q and Q' are independently selected from hydrogen and alkyl and alkenyl groups containing 1-40 carbons.

3. The process of claim 2 wherein R and R' are independently selected from alkyl, cycloalkyl, and aralkyl groups containing 3-8 carbons and Q and Q' are independently selected from hydrogen and alkyl and alkenyl groups containing 1-20 carbons.

4. The process of claim 2 wherein the 4-(1-alkenyl)-2,6-dihydrocarbylphenol is 1,1-dimethyl-2-(3,5-di-t-butyl-4-hydroxyphenyl)ethene.

5. The process of claim 1 wherein the oxygen-containing gas is oxygen.

6. The process of claim 1 wherein the oxygen-containing gas is air.

7. The process of claim 1 wherein the solvent is an alcohol contaning 1-10 carbons.

8. The process of claim 7 wherein the alcohol is a branched-chain alkanol.

9. The process of claim 8 wherein the alkanol is isopropyl alcohol.

10. The process of claim 8 wherein the alkanol is t-butyl alcohol.

11. The process of claim 1 wherein the catalyst is an alkali metal hydroxide.

12. The process of claim 11 wherein the catalyst is sodium hydroxide.

13. The process of claim 11 wherein the catalyst is potassium hydroxide.

14. The process of claim 1 wherein the catalyst is an alkaline earth metal hydroxide.

* * * * *